US012763205B2

(12) United States Patent
Nunally

(10) Patent No.: US 12,763,205 B2
(45) Date of Patent: Oct. 13, 2026

(54) SYSTEMS AND METHODS FOR AVATAR-BASED INTERACTIONS

(71) Applicant: Datum Point Labs Inc., Jackson, WY (US)

(72) Inventor: Patrick Nunally, San Diego, CA (US)

(73) Assignee: Datum Point Labs Inc.

( * ) Notice: Subject to any disclaimer, the term of this patent is extended or adjusted under 35 U.S.C. 154(b) by 166 days.

(21) Appl. No.: 18/582,404

(22) Filed: Feb. 20, 2024

(65) Prior Publication Data

US 2024/0339211 A1 Oct. 10, 2024

Related U.S. Application Data

(60) Provisional application No. 63/457,676, filed on Apr. 6, 2023.

(51) Int. Cl.

| | |
|---|---|
| ***G16H 40/67*** | (2018.01) |
| ***G06F 3/01*** | (2006.01) |
| ***G06F 3/04815*** | (2022.01) |
| ***G06T 13/00*** | (2011.01) |

(52) U.S. Cl.

CPC ............. *G16H 40/67* (2018.01); *G06F 3/017* (2013.01); *G06F 3/04815* (2013.01); *G06T 13/00* (2013.01); *G06T 2200/24* (2013.01); *G06T 2210/41* (2013.01)

(58) Field of Classification Search

None

See application file for complete search history.

(56) References Cited

U.S. PATENT DOCUMENTS

| | | | | |
|---|---|---|---|---|
| 11,109,815 | B2 * | 9/2021 | Schroeter | G16H 10/60 |
| 11,516,435 | B1 * | 11/2022 | Spindell | H04N 7/147 |
| 2014/0074454 | A1 * | 3/2014 | Brown | G10L 15/08<br>704/235 |
| 2024/0212826 | A1 * | 6/2024 | Shiloni | G06V 40/175 |
| 2024/0312625 | A1 * | 9/2024 | Bautista | G16H 20/00 |

OTHER PUBLICATIONS

Ali et al.; "Metaverse in Healthcare Integrated with Explainable AI and Blockchain: Enabling Immersiveness, Ensuring Trust, and Providing Patient Data Security;" Sensors 2023, 23, 565; MDPI, Basel, Switzerland; 17 pages; published Jan. 4, 2023 (Year: 2023).*

* cited by examiner

*Primary Examiner* — Edward Martello

(74) *Attorney, Agent, or Firm* — The Rapacke Law Group

(57) ABSTRACT

Embodiments described herein provide systems and methods for avatar-based interactions. A system receives, via a user interface device, a first user input including one or more of an audio input, a text input, or a video input. The system generates, based on a trained model, a first response to the first user input. The system renders a virtual avatar model based on the first response. The system receives a second user input via the user interface device. The system determines, based on the second user input, to provide an advanced level of care including: control a communication link between the computing device and a credentialed service device, receive a second response to the second user input from the credentialed service device via the communication link, and render the virtual avatar model based on the second response.

20 Claims, 7 Drawing Sheets

SYSTEMS AND METHODS FOR AVATAR-BASED INTERACTIONS

CROSS REFERENCE(S)

The instant application is a nonprovisional of and claim priority under 35 U.S.C. 119 to U.S. provisional application No. 63/457,676, filed Apr. 6, 2023, which is hereby expressly incorporated by reference herein in its entirety.

TECHNICAL FIELD

The embodiments relate generally to systems and methods for avatar-based interactions.

BACKGROUND

In many cases, the provision of adequate healthcare has been complicated due to the lack of sufficient number of medical professionals, the complexities associated with continuity of care, the social difficulties of gender in medical care, social stigmas of certain medical conditions, and the geographical distance from. patients. Current technologies have not been capable of providing care to patients as automated systems comes with legal and regulatory challenges, including issues related to liability, accountability, and ensuring patient privacy. Legal frameworks for patient care create clear delineations between medical data gathering, basic medical information, the right to provide medical advice, the right to prescribe medications have limited the ability to support healthcare needs. The fact that qualified and competent personal private doctors are increasingly in short supply, overbooked or are physically in accessible in a timely way has driven emergency room visits up increasing the cost of typical consultation by 1200%—these issues as well as the frequency of data gathering, and patient interaction have become significant barriers to achieving material levels of patient care through telemedicine processes of the prior art. Similar limitations exist in other domains where experts are in demand (e.g., Financial, Educational, Counselors, Therapists, Legal and other professionals.) Therefore, there is a need for improved systems and methods for a uniform avatar-based providing user interactions provided by an AI service agent, a remote human professional service provider, or a combination of both AI and human professional based on the needs dictated by the interaction.

DETAILED DESCRIPTION

Figure 1:
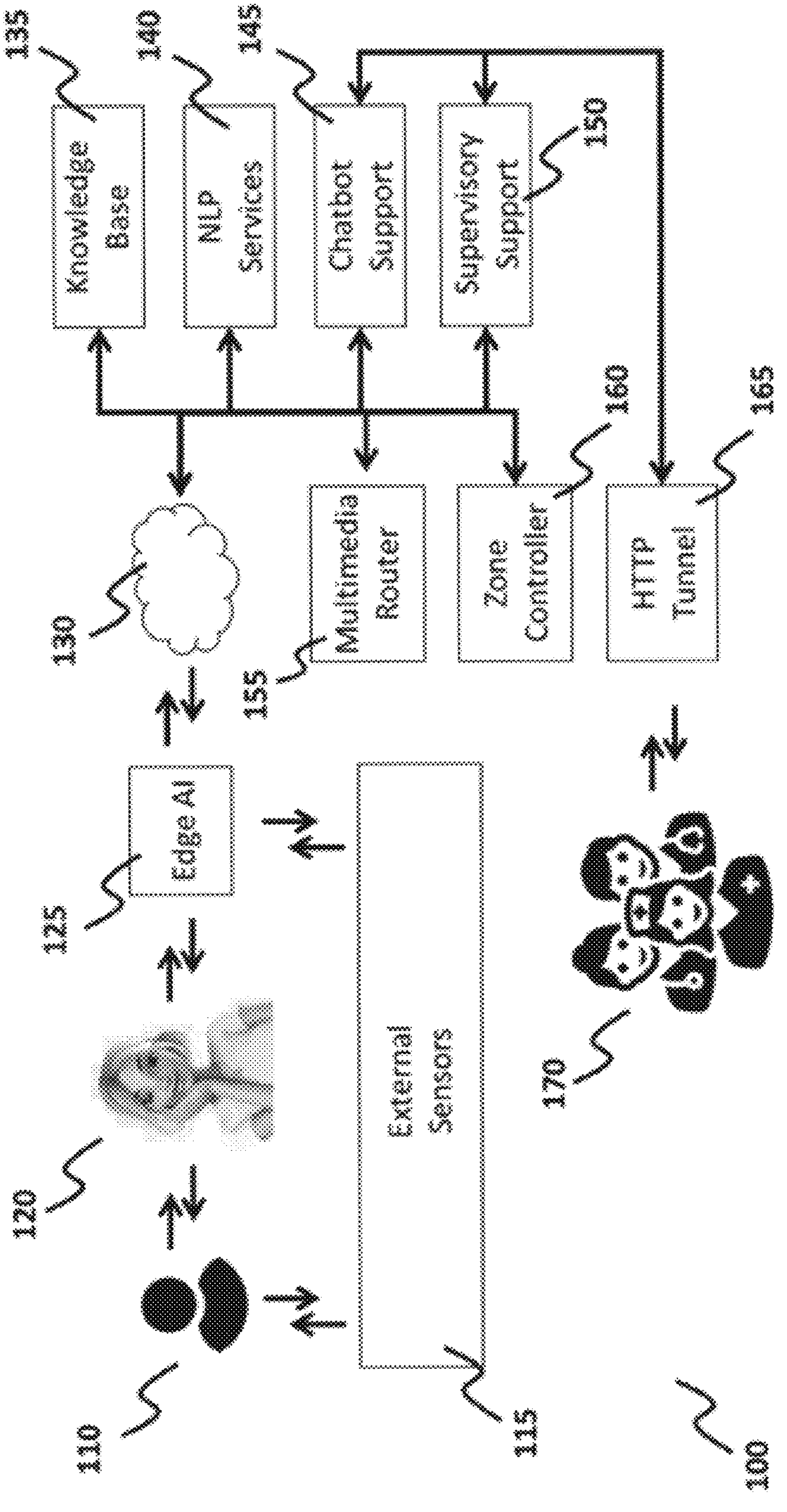
FIG. 1 illustrates a framework for avatar-based interactions, according to some embodiments.

In many cases, the provision of adequate healthcare has been complicated due to the lack of sufficient number of medical professionals located in proximity to the patients. Advanced digital/mobile technology providing low-cost connectivity and computer power has enabled the option of large-scale telemedicine and advanced cloud-based systems are being deployed. These systems enable a variety of care to be delivered to patients conveniently and cost-effectively using local systems and attendants and remote doctors using video conferencing.

The current focus in the art has been on expanding the deployment of these systems and attracting a large flow of patients (the demand side). Current technologies have not been capable of providing anthropomorphized continuity of care allowing machine as well as an array of supply side services to be provided through the users anthropomorphized character allowing patients to be largely free of social, sexual, lifestyle, and other stigmas. The fact that qualified and competent personal private doctors are increasingly in short supply, overbooked or are physically inaccessible in a timely way has driven emergency room visits up increasing the cost of typical consultation by 1200%—these issues as well as the frequency of data gathering, and patient interaction have become significant barriers to achieving material levels of patient care through telemedicine processes of the prior art.

In light of current technology there is a critical need for a system and method capable of transcending the array of needs of patient care, specifically where patients need a greater experience of care continuity, frequency of interactions and data gathering, an anthropomorphized (i.e., avatar) animated interface to eliminate personal and social stigma, as well as selective support of the patient through the common animated interface where an array of machines, social, administrative, medical professional and other parties can interact, gather data, analysis data, provide medical services, write prescriptions, order tests and other patient centric medical services.

One or more implementations of the present application provide a full array of medical services to specific patients. This system and method is supported by a combination of edge services in support of emotional, graphical, audio and in some cases text of the patient facing animated persona. This system is supported by a full suite of sensor data gathering including wirelessly connected sensors, camera interface to support its use as a sensor for patient analysis, natural language processing, native security and in some cases alternative communication support for patients who can't or would prefer not to speak.

In some embodiments, the patient interface is a mobile device such as a mobile smartphone, tablet, vehicle or in some cases a fixed computational device (e.g., a kiosk, desktop, etc.,). The systems and methods described here also include a backend triage of services including but not limited to AI systems to provide uniform user interface and perceived continuity of service, a scheduled interaction capacity to regularly interact with the patient and prompt the patient to provide input, discuss data, gather symptom description, answer questions, access mental status, gauge pain level, medication compliance, mobility and other key indicators of patient wellbeing. The system additionally routes questions or active interaction (as indicated) to medical or support services as needed. When routed the patient is not overtly told that the animated avatar may at any time be driven by one or more AI agents, medical professionals or support services staff actively communicating through the guise of the said anthropomorphized animated avatar thus forming the basis of a full range of services being provided to the patient through the avatar.

In some embodiments, systems described herein use a unique edge animated avatar which is used to provide patient care offered from a root AI driven interface (selected from one or more audio, video, graphic, VR, AR) and can act as a common avatar driven as needed by an array of human medical professionals, support services as required or multiparty participation. While AI can be effective at gathering and evaluation of some levels of data collection, more complex medical diagnosis, qualitative evaluation provision of pharmaceuticals, and other key services require credentials to be provided. Systems described herein allow medical professionals to seamlessly host telemedicine appointments on an ad-hoc basis. Scheduling with a family doctor can at times require weeks of waiting, often requiring an emergency room visit for lack of access to medical services. By using a common avatar, a patient can receive telemedicine support from medical professionals who may simply be the next available but still maintain the perception of continuity of care.

Systems and methods described herein include, for example, secure edge animated avatar supported conditionally by one or more AI patient services engine coupled to a knowledge base including relevant generative models as well as directed models supporting patient interactions, data gathering and assessment of patient. Patient continuity of care may be provided as the avatar can be driven by automated processes for routine wellness checks of the patient however the avatar can be seamlessly driven by a medical professional enabling a full range of telemedicine and support services all through the established avatar so patients always have a common interface independent of the medical or service professionals available to support the patient. Systems described herein may interface to a secure ledger for storing wellness check and sensor data into an ongoing patient history so that AI agents, service providers as well as medical professionals can securely access patient records and store medical reports, treatment plans, prescriptions written as well as billing and support data as needed. Systems described herein may be compatible with existing mobile devices and communication infrastructures.

Embodiments described herein provide a number of benefits. For example, providing an animated avatar interface may allow for a user (e.g., a patient) to have seamless continuity of care, as the avatar interface may be controlled via a generative AI model or models and/or knowledge bases when that is adequate, and may be controlled by a credentialed user (e.g., a doctor) as the need arises. This may be further enhanced by modifying or transcoding the credentialed user's voice to match the avatar voice which normally interacts with the patient, such that the credentialed user may provide natural vocal responses without sacrificing the continuity of the avatar interface. Information gathered via the avatar interface before connecting to a credentialed user may be provided to the credentialed user, thereby providing an efficient interface and mechanism for collecting user information, including sensitive user information, without the need to repeat or re-enter the information. User information may also be summarized by the system, requiring less data to be transmitted and displayed to the credentialed user.

In one preferred embodiment an avatar nurse can provide a wide range of services to patients. In addition to providing remote patient monitoring and assessment of acute and chronic patient wellbeing, avatar nurses can also provide education, support, and resources. Avatar nurses can take the time needed to gather complete datasets throughout the day, provide patient guidance as well as reinforce and encourage prescribed regiments. In addition, avatar nurses can aid caregivers with record keeping as well as mood and activity level assessments. As required by AI determination, and or patient request the avatar may seamlessly transition to professional medical services (this may take the form of the avatar visage still presenting but a medical professional actually doing the live patient interaction allowing a group of doctors/nurses to support a patient without breaking the patients view of continuity of care or social issue avoidance), and provide support for caregivers.

In yet another embodiment, Avatar nurses can provide valuable support and guidance for new mothers. They can help with everything from breastfeeding to bonding with their new baby. In addition, avatar nurses can provide education on newborn care and answer any questions parents may have. Avatar nurses can also classify mood and fatigue patterns to provide postpartum support including seamless medical assessment for post partum issues, support, guidance and specialist support for key topics like lactation including help with recovery and adjusting to life with a new baby and even body image issues and sexual health. In yet another embodiment, Patients with chronic conditions can benefit from the continuity of care provided by avatar nurses. Because avatar nurses get to know their patients well, they can provide more personalized care. In addition, avatar nurses can help patients manage their conditions and prevent complications. For example, an avatar nurse might teach a patient with diabetes how to monitor their blood sugar levels and give them tips for healthy eating. Besides providing patient education, avatar nurses can also coordinate care with other healthcare team members. This is especially important for people with chronic conditions who see multiple specialists. In all cases the avatar nurse presented may actually be a range of medical service providers or the local AI avatar but in all cases the local AI can provided the answers and guidance the patient needs or connect the patient to the service they need while always maintaining the patient relationship and sense of privacy.

In another embodiment this system and method supports patient needs after surgery, patients often need help with assessment of their recovery, AI nurses can provide these services and help patients with their overall recovery. For example, avatar nurses might teach patients exercises to improve their strength and range of motion. In addition, AI nurses can provide support and education on managing pain, which is an integral part of recovery. However, Kai care for post-operative patients is not just about physical recovery but also mental and emotional recovery. Kai nurses can provide emotional support and help patients adjust to their new reality.

FIG. 1 illustrates an exemplary framework 100 for avatar-based interactions, according to some embodiments. Framework 100 illustrates a user 110 (e.g., a medical patient) employing a local interface device supported by a user interface avatar 120 which may be provided via a user interface device (e.g., mobile device, desktop computer, laptop, kiosk, etc.). A local processing system 125 may be provided for performing edge processing in communication with one or more wired or wireless networks, one of which is a cloud network 130 and optionally a local area network in communication with sensors 115. Sensors 115 may gather one or more data sets relative to the user 110 (e.g., video, audio, text input, temperature sensors, etc.). In some embodiments, sensors 115 may be utilized at specific times as determined by the system or as instructed by a credentialed user 170. For example, if a credentialed user 170 determines that a temperature should be taken of user 120, they may request the temperature sensor data. In another example, baseline measurements (e.g., temperature, blood pressure, etc.) may be retrieved by the system without a request from a credentialed user 170. For example, a user 120 may interact with the system daily, and each day the system may make a blood pressure measurement based on a predefined care plan. In response to a blood pressure measurement (or any other sensor measurement) exceeding a threshold, the system may determine to provide an enhanced level of care by connecting to a credentialed user 170 as described herein.

User 110 may be supported by said avatar 120 as their primary interface to services (e.g., medical services) through Natural Language Services 140 as well as chatbot support 145 each of which may be driven and supported in part by a knowledge base 135. Knowledge base 135 may include domain-specific information (e.g., medical knowledge) and/or historical information associated with user 120 (e.g., identifying information, medical history, chat history, etc.). As appropriate or by request of said patient 110, certain operations cannot be legally supported by the AI system knowledge base (i.e., requires medical professional credentials, prescription authority, etc.) and are routed via multimedia router 155 to an available qualified (credentialed) user 170 by zone controller 160 via a private channel 165 such that the avatar 120 remains the interface to the patient 110 and while the avatar retains its persona the credentialed user (e.g., medical professional) 170 is performing a telemedicine function.

In some embodiments, zone controller 160 selects the credentialed user 170 based on a location. For example, there may be a restriction that the credentialed user 170 be from the same state (e.g., based on a legal regulation) or some other predefined region, and zone controller 160 selects a credentialed user 170 from a list of credentialed users based on this restriction. In some embodiments, zone controller 160 selects the credentialed user 170 based on proximity to edge device 125 or proximity to a server (e.g., multimedia router 155) in order to reduce latency.

In some embodiments, the interface provided to credentialed user 170 is not avatar-based, but rather the credentialed user 170 is able to see and hear user 120 as captured by sensors 115. In this way, credentialed user 170 may interact with user 120 as if over a normal voice call or video call, while user 120 experiences the interaction via an avatar based interface. This may reduce the amount of generating and/or rendering required to be performed by the system, and allow for the credentialed user 170 to see an accurate representation of user 120 which may be important (e.g., in diagnosing an illness).

In framework 100, the user 120 perceives anonymity, lower social anxiety and receives a full range of medical services from AI driven wellness checks to complex medical diagnosis, emotional support and pharmaceutical services through their familiar animated avatar. While examples herein describe a medical use-case, the systems and methods described herein may be utilized in a number of different ways. For example, a user may interact with the system to get advice in performing motor vehicle maintenance, and may get automatically generated responses, or may be connected to a professional mechanic. Other subject matter areas where there are people with specialized knowledge may utilize systems described herein.

Figure 2:
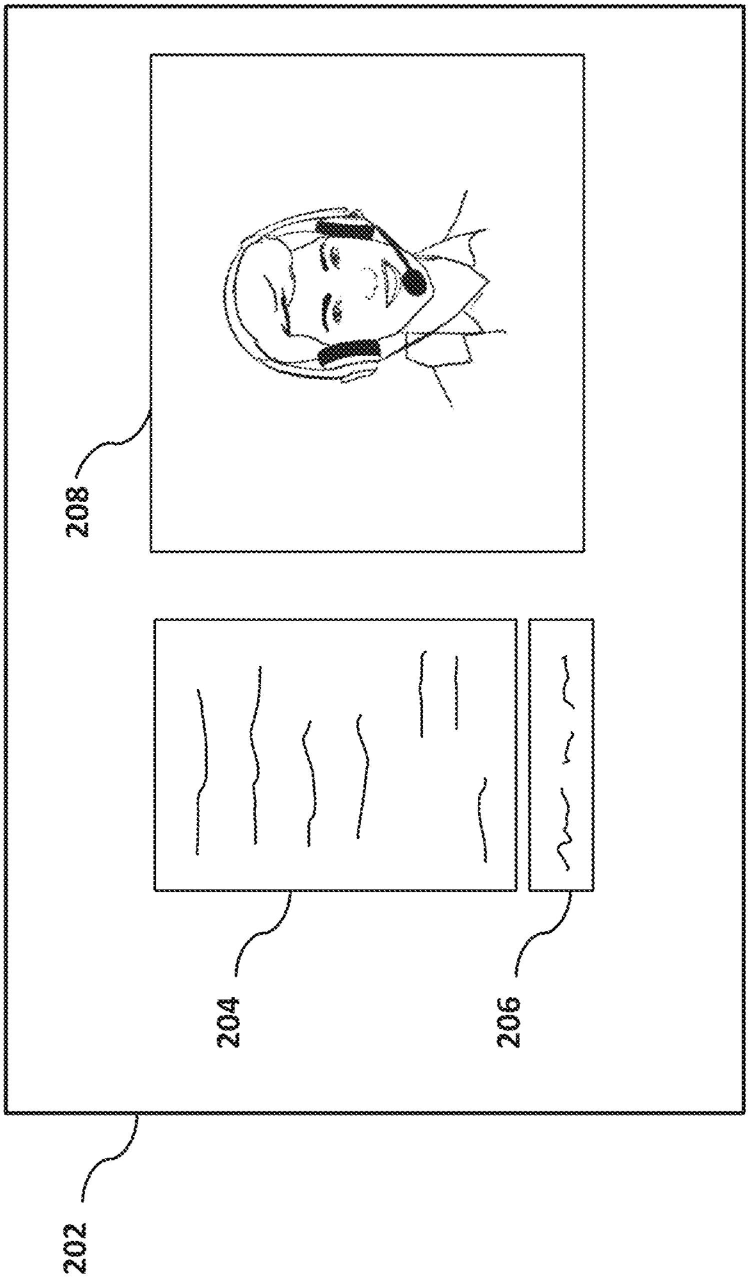
FIG. 2 illustrates a user interface for avatar-based interactions, according to some embodiments.

FIG. 2 illustrates a user interface 202 for avatar-based interactions, according to some embodiments. User interface 202 may include an avatar display window 208 for displaying the generated avatar 120. A user may interact with the avatar, for example, by entering text into text box 206, with chat history displayed in chat history box 204. A User may, in some embodiments, interact with avatar 208 by using voice and gestures, as captured via sensors 115 (e.g., camera and microphone sensors). As discussed in FIG. 1, the avatar displayed in avatar window 208 may be rendered with automatically generated gestures, voice, and/or text.

In response to a user input (e.g., asking or answering a question), the system (locally or via a remote device via a network) may generate a text, audio and/or video response. The system may determine based on user input, sensor data gathered or timing of key interactions to change control of the avatar to a credentialed user. For example, the system may determine that a patients questions may require a medication change, the patients speech is slurred compared to the patients baseline, or a diagnosis of a condition is required, so an expert is needed to respond. In another example, the user input may indicate a sensitive or urgent response is required (e.g., an urgent medical issue). In another example, the user indicates explicitly the desire to be connected to a credentialed user. Avatar window 208 may also be used to display information retrieved and/or generated by the system as a visual aid to a response by the avatar. For example, a diagram may be displayed in order to describe a medical issue.

When connected to a credentialed user, the avatar displayed in avatar window 208 may be configured to mimic the gestures and/or words of the credentialed user. The credentialed user may connect via a user interface device that includes sensors (e.g., microphone and/or video sensors). If the credentialed user makes different facial expressions (e.g., surprise, concern, curiosity), the avatar may mimic those expressions, but with the appearance of the avatar already established. If the credentialed user interacts via text input, text-to-speech generation may be performed using a speech style already established for the avatar. If the credentialed user interacts via speaking into a microphone, the credentialed user's voice may be modified or transcoded to match the voice of the avatar. For example, if the avatar is a man with a low voice, and the credentialed user is a female with a high voice, the avatar as presented to the user may be generated to say the same things as the credentialed user with the same cadence, but in a low voice matching the already established voice style. This may provide a level of anonymity that makes the user experience consistent between automatically generated responses and credentialed user responses, which has a demonstrated ability to provide the user with a greater sense of anonymity, a continuity of care as the avatar is their familiar medical reference point and putting the user at ease.

Figure 3:
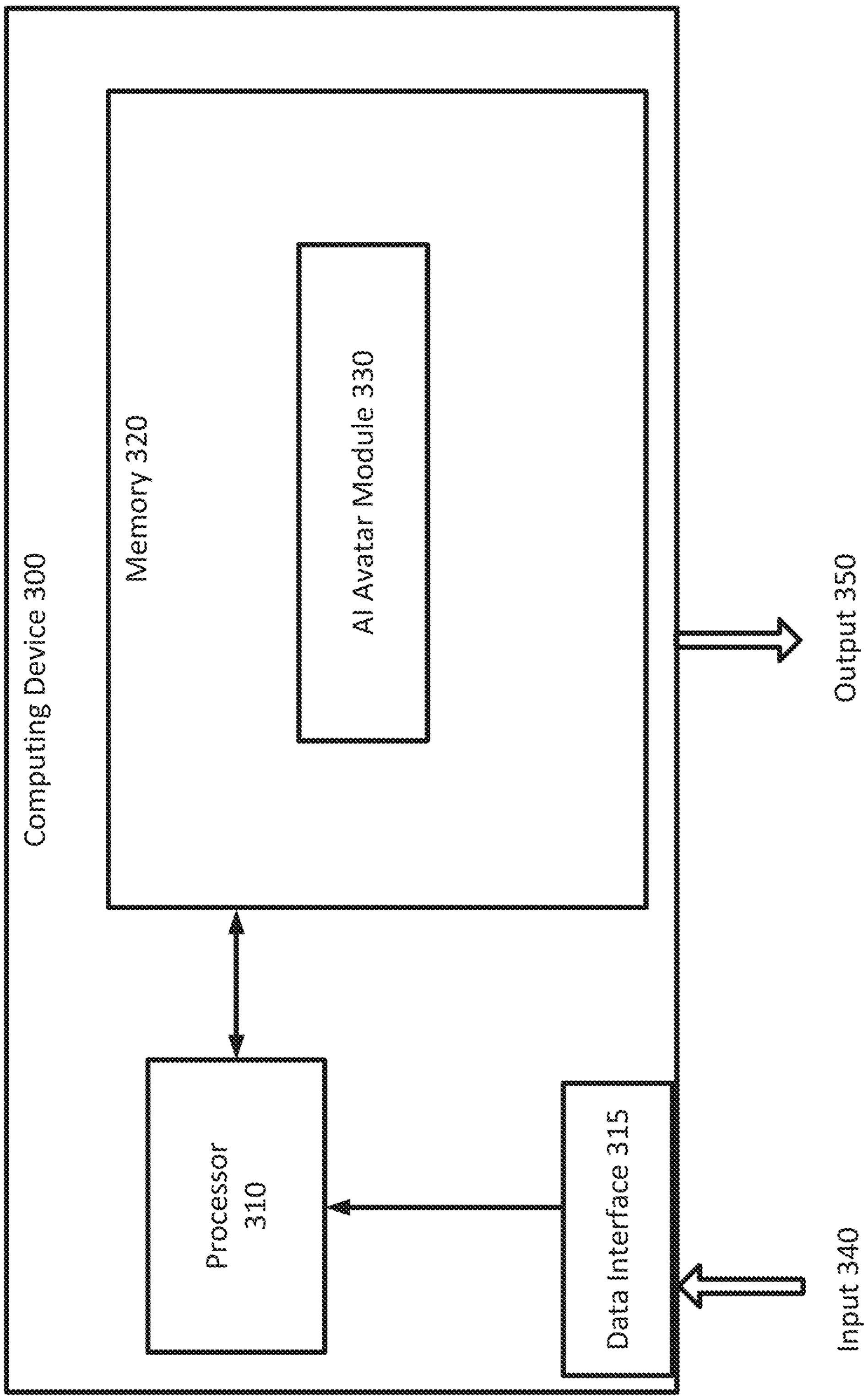
FIG. 3 is a simplified diagram illustrating a computing device implementing the framework described herein, according to some embodiments.

FIG. 3 is a simplified diagram illustrating a computing device 300 implementing the framework described herein, according to some embodiments. As shown in FIG. 3, computing device 300 includes a processor 310 coupled to memory 320. Operation of computing device 300 is controlled by processor 310. And although computing device 300 is shown with only one processor 310, it is understood that processor 310 may be representative of one or more central processing units, multi-core processors, microprocessors, microcontrollers, digital signal processors, field programmable gate arrays (FPGAs), application specific integrated circuits (ASICs), graphics processing units (GPUs) and/or the like in computing device 300. Computing device 300 may be implemented as a stand-alone subsystem, as a board added to a computing device, and/or as a virtual machine.

Memory 320 may be used to store software executed by computing device 300 and/or one or more data structures used during operation of computing device 300. Memory 320 may include one or more types of transitory or non-transitory machine-readable media (e.g., computer-readable media). Some common forms of machine-readable media may include floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, and/or any other medium from which a processor or computer is adapted to read.

Processor 310 and/or memory 320 may be arranged in any suitable physical arrangement. In some embodiments, processor 310 and/or memory 320 may be implemented on a same board, in a same package (e.g., system-in-package), on a same chip (e.g., system-on-chip), and/or the like. In some embodiments, processor 310 and/or memory 320 may include distributed, virtualized, and/or containerized computing resources. Consistent with such embodiments, processor 310 and/or memory 320 may be located in one or more data centers and/or cloud computing facilities.

In some examples, memory 320 may include non-transitory, tangible, machine readable media that includes executable code that when run by one or more processors (e.g., processor 310) may cause the one or more processors to perform the methods described in further detail herein. For example, as shown, memory 320 includes instructions for AI avatar module 330 that may be used to implement and/or emulate the systems and models, and/or to implement any of the methods described further herein.

AI avatar module 330 may receive input 340 such as user input, sensor data, text, etc. and generate an output 350 such as a response provided via an avatar. For example, AI avatar module 330 may be configured to generate a response using language generation (e.g., via a large language model), retrieval from a database or knowledge base, etc., and may present the generated response via an avatar by rendering the avatar with gestures and voice generated based on the generated response.

The data interface 315 may comprise a communication interface, a user interface (such as a voice input interface, a graphical user interface, and/or the like). For example, the computing device 300 may receive the input 340 from a networked device via a communication interface. Or the computing device 300 may receive the input 340, such as a spoken question, from a user via the user interface.

Some examples of computing devices, such as computing device 300 may include non-transitory, tangible, machine readable media that include executable code that when run by one or more processors (e.g., processor 310) may cause the one or more processors to perform the processes of method. Some common forms of machine-readable media that may include the processes of method are, for example, floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, and/or any other medium from which a processor or computer is adapted to read.

Figure 4:
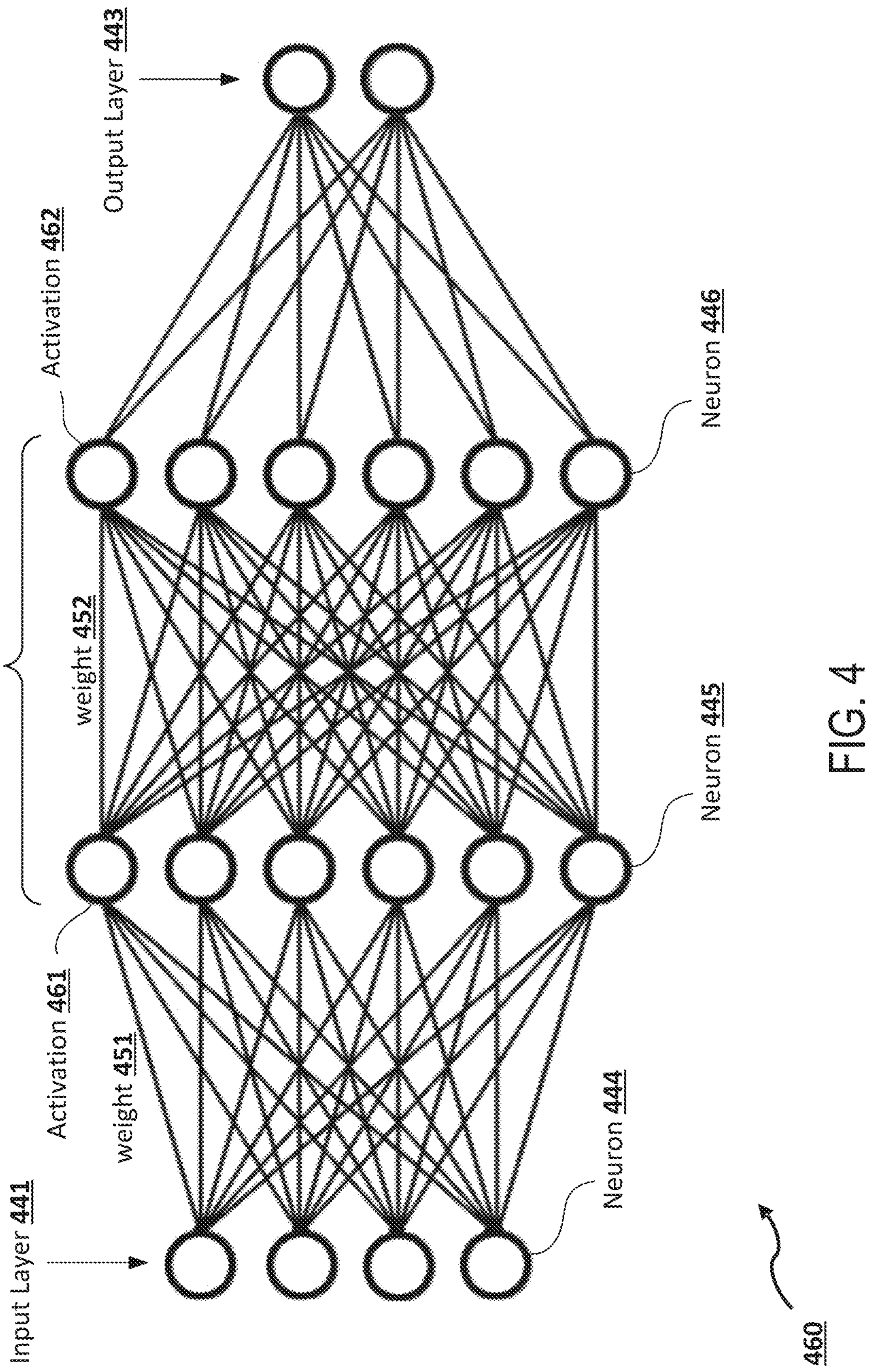
FIG. 4 is a simplified diagram illustrating a neural network structure, according to some embodiments.

FIG. 4 is a simplified diagram illustrating the neural network structure, according to some embodiments. In some embodiments, the AI avatar module 330 may be implemented at least partially via an artificial neural network structure shown in FIG. 4. The neural network comprises a computing system that is built on a collection of connected units or nodes, referred to as neurons (e.g., 444, 445, 446). Neurons are often connected by edges, and an adjustable weight (e.g., 451, 452) is often associated with the edge. The neurons are often aggregated into layers such that different layers may perform different transformations on the respective input and output transformed input data onto the next layer.

For example, the neural network architecture may comprise an input layer 441, one or more hidden layers 442 and an output layer 443. Each layer may comprise a plurality of neurons, and neurons between layers are interconnected according to a specific topology of the neural network topology. The input layer 441 receives the input data such as training data, user input data, vectors representing latent features, etc. The number of nodes (neurons) in the input layer 441 may be determined by the dimensionality of the input data (e.g., the length of a vector of the input). Each node in the input layer represents a feature or attribute of the input.

The hidden layers 442 are intermediate layers between the input and output layers of a neural network. It is noted that two hidden layers 442 are shown in FIG. 4 for illustrative purpose only, and any number of hidden layers may be utilized in a neural network structure. Hidden layers 442 may extract and transform the input data through a series of weighted computations and activation functions.

For example, as discussed in FIG. 3, the AI avatar module 330 receives an input 340 and transforms the input into an output 350. To perform the transformation, a neural network such as the one illustrated in FIG. 4 may be utilized to perform, at least in part, the transformation. Each neuron receives input signals, performs a weighted sum of the inputs according to weights assigned to each connection (e.g., 451, 452), and then applies an activation function (e.g., 461, 462, etc.) associated with the respective neuron to the result. The output of the activation function is passed to the next layer of neurons or serves as the final output of the network. The activation function may be the same or different across different layers. Example activation functions include but not limited to Sigmoid, hyperbolic tangent, Rectified Linear Unit (ReLU), Leaky ReLU, Softmax, and/or the like. In this way, after a number of hidden layers, input data received at the input layer 441 is transformed into rather different values indicative data characteristics corresponding to a task that the neural network structure has been designed to perform.

The output layer 443 is the final layer of the neural network structure. It produces the network's output or prediction based on the computations performed in the preceding layers (e.g., 441, 442). The number of nodes in the output layer depends on the nature of the task being addressed. For example, in a binary classification problem, the output layer may consist of a single node representing the probability of belonging to one class. In a multi-class classification problem, the output layer may have multiple nodes, each representing the probability of belonging to a specific class.

Therefore, the AI avatar module 330 may comprise the transformative neural network structure of layers of neurons, and weights and activation functions describing the non-linear transformation at each neuron. Such a neural network structure is often implemented on one or more hardware processors 310, such as a graphics processing unit (GPU).

In one embodiment, the AI avatar module 330 may be implemented by hardware, software and/or a combination thereof. For example, the AI avatar module 330 may comprise a specific neural network structure implemented and run on various hardware platforms 460, such as but not limited to CPUs (central processing units), GPUs (graphics processing units), FPGAs (field-programmable gate arrays), Application-Specific Integrated Circuits (ASICs), dedicated AI accelerators like TPUs (tensor processing units), and specialized hardware accelerators designed specifically for the neural network computations described herein, and/or the like. Example specific hardware for neural network structures may include, but not limited to Google Edge TPU, Deep Learning Accelerator (DLA), NVIDIA AI-focused GPUs, and/or the like. The hardware 460 used to implement the neural network structure is specifically configured based on factors such as the complexity of the neural network, the scale of the tasks (e.g., training time, input data scale, size of training dataset, etc.), and the desired performance.

In one embodiment, the neural network based AI avatar module 330 may be trained by iteratively updating the underlying parameters (e.g., weights 451, 452, etc., bias parameters and/or coefficients in the activation functions 461, 462 associated with neurons) of the neural network based on a loss function. For example, during forward propagation, the training data such as user questions are fed into the neural network. The data flows through the network's layers 441, 442, with each layer performing computations based on its weights, biases, and activation functions until the output layer 443 produces the network's output 450. In some embodiments, output layer 443 produces an intermediate output on which the network's output 450 is based.

The output generated by the output layer 443 is compared to the expected output (e.g., a "ground-truth" such as the corresponding response to the input question) from the training data, to compute a loss function that measures the discrepancy between the predicted output and the expected output. Given a loss function, the negative gradient of the loss function is computed with respect to each weight of each layer individually. Such negative gradient is computed one layer at a time, iteratively backward from the last layer 443 to the input layer 441 of the neural network. These gradients quantify the sensitivity of the network's output to changes in the parameters. The chain rule of calculus is applied to efficiently calculate these gradients by propagating the gradients backward from the output layer 443 to the input layer 441.

Parameters of the neural network are updated backwardly from the last layer to the input layer (backpropagating) based on the computed negative gradient using an optimization algorithm to minimize the loss. The backpropagation from the last layer 443 to the input layer 441 may be conducted for a number of training samples in a number of iterative training epochs. In this way, parameters of the neural network may be gradually updated in a direction to result in a lesser or minimized loss, indicating the neural network has been trained to generate a predicted output value closer to the target output value with improved prediction accuracy. Training may continue until a stopping criterion is met, such as reaching a maximum number of epochs or achieving satisfactory performance on the validation data. At this point, the trained network can be used to make predictions on new, unseen data, such as unseen user questions.

Neural network parameters may be trained over multiple stages. For example, initial training (e.g., pre-training) may be performed on one set of training data, and then an additional training stage (e.g., fine-tuning) may be performed using a different set of training data. In some embodiments, all or a portion of parameters of one or more neural-network model being used together may be frozen, such that the "frozen" parameters are not updated during that training phase. This may allow, for example, a smaller subset of the parameters to be trained without the computing cost of updating all of the parameters.

The neural network illustrated in FIG. 4 is exemplary. For example, different neural network structures may be utilized, and additional neural-network based or non-neural-network based component may be used in conjunction as part of module 330. For example, a text input may first be embedded by an embedding model, a self-attention layer, etc. into a feature vector. The feature vector may be used as the input to input layer 441. Output from output layer 443 may be output directly to a user or may undergo further processing. For example, the output from output layer 443 may be decoded by a neural network based decoder. The neural network illustrated in FIG. 400 and described herein is representative and demonstrates a physical implementation for performing the methods described herein.

Through the training process, the neural network is "updated" into a trained neural network with updated parameters such as weights and biases. The trained neural network may be used in inference to perform the tasks described herein, for example those performed by module 330. The trained neural network thus improves neural network technology in user interaction.

Figure 5:
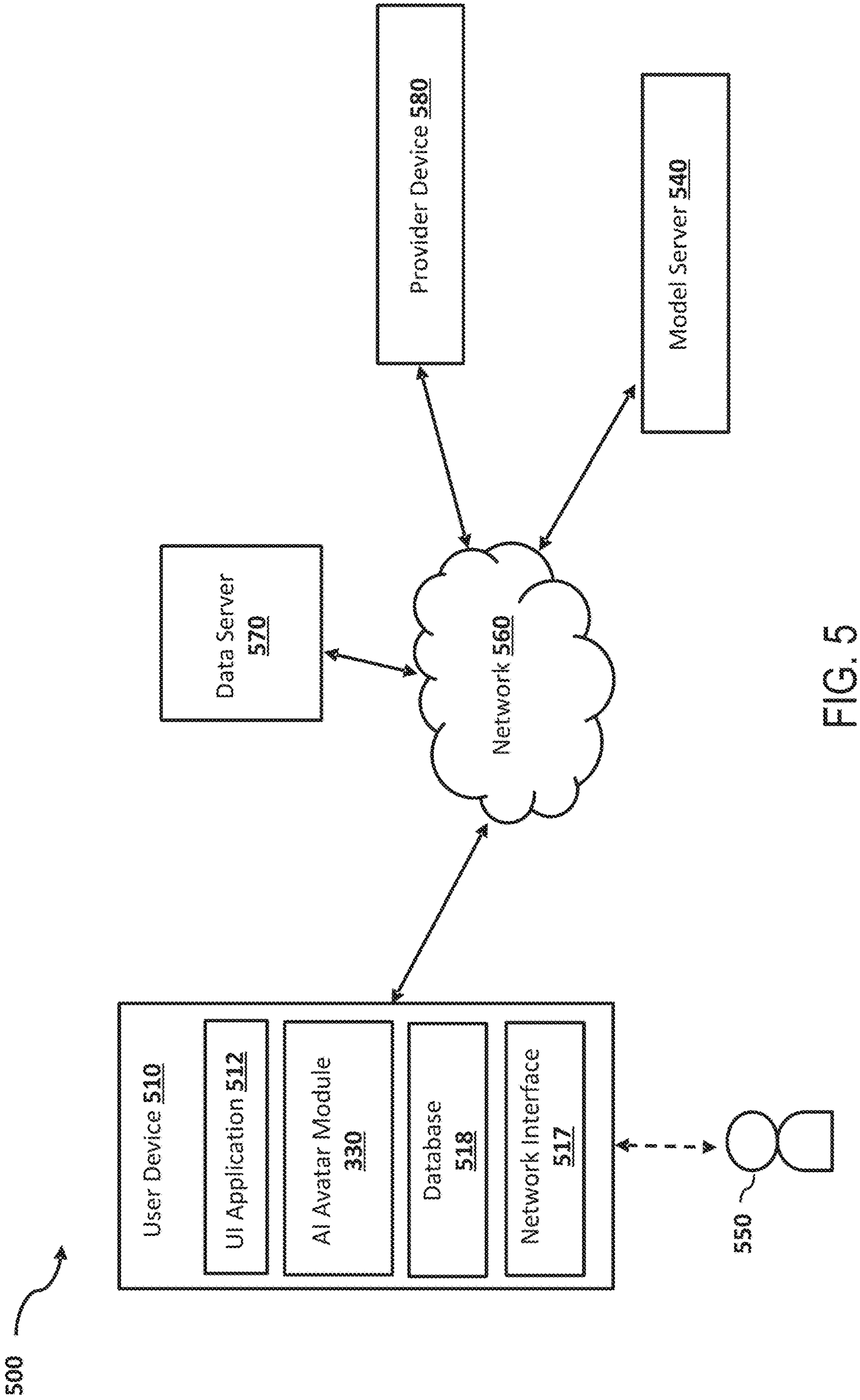
FIG. 5 is a simplified block diagram of a networked system suitable for implementing the framework described herein.

FIG. 5 is a simplified block diagram of a networked system 500 suitable for implementing the framework described herein. In one embodiment, system 500 includes the user device 510 (e.g., computing device 300) which may be operated by user 550, data server 570, model server 540, and other forms of devices, servers, and/or software components that operate to perform various methodologies in accordance with the described embodiments. Exemplary devices and servers may include device, stand-alone, and enterprise-class servers which may be similar to the computing device 300 described in FIG. 3, operating an OS such as a MICROSOFT® OS, a UNIX® OS, a LINUX® OS, a real-time operation system (RTOS), or other suitable device and/or server-based OS. It can be appreciated that the devices and/or servers illustrated in FIG. 5 may be deployed in other ways and that the operations performed, and/or the services provided by such devices and/or servers may be combined or separated for a given embodiment and may be performed by a greater number or fewer number of devices and/or servers. One or more devices and/or servers may be operated and/or maintained by the same or different entities. In some embodiments, user device C10 is used in training neural network based models. In some embodiments, user device C10 is used in performing inference tasks using pre-trained neural network based models (locally or on a model server such as model server 540).

User device 510, data server 570, and model server 540 may each include one or more processors, memories, and other appropriate components for executing instructions such as program code and/or data stored on one or more computer readable mediums to implement the various applications, data, and steps described herein. For example, such instructions may be stored in one or more computer readable media such as memories or data storage devices internal and/or external to various components of system 500, and/or accessible over network 560. User device 510, data server 570, and/or model server 540 may be a computing device 300 (or similar) as described herein.

In some embodiments, all or a subset of the actions described herein may be performed solely by user device 510. In some embodiments, all or a subset of the actions described herein may be performed in a distributed fashion by various network devices, for example as described herein.

User device 510 may be implemented as a communication device that may utilize appropriate hardware and software configured for wired and/or wireless communication with data server 570 and/or the model server 540. For example, in one embodiment, user device 510 may be implemented as an autonomous driving vehicle, a personal computer (PC), a smart phone, laptop/tablet computer, wristwatch with appropriate computer hardware resources, eyeglasses with appropriate computer hardware (e.g., GOOGLE GLASS®), other type of wearable computing device, implantable communication devices, and/or other types of computing devices capable of transmitting and/or receiving data, such as an IPAD® from APPLE®. Although only one communication device is shown, a plurality of communication devices may function similarly.

User device 510 of FIG. 5 contains a user interface (UI) application 512, and AI avatar module 330, which may correspond to executable processes, procedures, and/or applications with associated hardware. For example, the user device 510 may allow a user to interact via an avatar interface to receive responses either generated and/or as provided by a credentialed user. In other embodiments, user device 510 may include additional or different modules having specialized hardware and/or software as required.

In various embodiments, user device 510 includes other applications as may be desired in particular embodiments to provide features to user device 510. For example, other applications may include security applications for implementing client-side security features, programmatic client applications for interfacing with appropriate application programming interfaces (APIs) over network 560, or other types of applications. Other applications may also include communication applications, such as email, texting, voice, social networking, and IM applications that allow a user to send and receive emails, calls, texts, and other notifications through network 560.

Network 560 may be a network which is internal to an organization, such that information may be contained within secure boundaries. In some embodiments, network 560 may be a wide area network such as the internet. In some embodiments, network 560 may be comprised of direct physical connections between the devices. In some embodiments, network 560 may represent communication between different portions of a single device (e.g., a communication bus on a motherboard of a computation device).

Network 560 may be implemented as a single network or a combination of multiple networks. For example, in various embodiments, network 560 may include the Internet or one or more intranets, landline networks, wireless networks, and/or other appropriate types of networks. Thus, network 560 may correspond to small scale communication networks, such as a private or local area network, or a larger scale network, such as a wide area network or the Internet, accessible by the various components of system 500.

User device 510 may further include database 518 stored in a transitory and/or non-transitory memory of user device 510, which may store various applications and data (e.g., model parameters) and be utilized during execution of various modules of user device 510. Database 518 may store medical knowledge (e.g., symptoms of various diseases), user history, chat history, model parameters, etc. In some embodiments, database 518 may be local to user device 510. However, in other embodiments, database 518 may be external to user device 510 and accessible by user device 510, including cloud storage systems and/or databases that are accessible over network 560 (e.g., on data server 570).

User device 510 may include at least one network interface component 517 adapted to communicate with data server 570 and/or model server 540. In various embodiments, network interface component 517 may include a DSL (e.g., Digital Subscriber Line) modem, a PSTN (Public Switched Telephone Network) modem, an Ethernet device, a broadband device, a satellite device and/or various other types of wired and/or wireless network communication devices including microwave, radio frequency, infrared, Bluetooth, and near field communication devices.

Data Server 570 may perform some of the functions described herein. For example, data server 570 may store a training dataset including question/response pairs, etc. Data server 570 may provide data to user device 510 and/or model server 540. For example, training data may be stored on data server 570 and that training data may be retrieved by model server 540 while training a model stored on model server 540.

Model server 540 may be a server that hosts models described herein. Model server 540 may provide an interface via network 560 such that user device 510 may perform functions relating to the models as described herein (e.g., a large language model, a domain-specific neural network based model for responding to user input, a gesture generation model, a text-to-speech model, a voice conversion model, etc.). Model server 540 may communicate outputs of the models to user device 510 via network 560. User device 510 may display model outputs, or information based on model outputs, via a user interface to user 550. Models on model server 540 may retrieve information from data server 570 and/or database 518, for example to generate a response (e.g., retrieval augmented generation). In some embodiments, data server 570 and model server 540 may be the same device or co-located. In some embodiments, some or all of the functions provided by data server 570 and/or model server 540 may be performed by user device 510.

Provider device 580 may be used by a credentialed user in order to interact with a user 550 via AI avatar module 330. In some embodiments, provider device 580 may receive user information (e.g., medical history, chat history, summarized history, etc.) from user device 510, data server 570, and/or model server 540. For example, model server 540 may include a summarization model that may summarize the chat history stored on data server 570, and provide the summarized information to provider device 580. For example, a medical professional may use user provider device 580 which may include a camera sensor and a microphone sensor, such that the gestures and voice of the credentialed user may be transmitted via network 560 to user device 510. Information (e.g., voice and gestures) from provider device 580 may be transmitted first to model server 540 via network 560 so that models on model server 540 may adapt the information to the avatar interface (e.g., by performing voice conversion, and avatar gesture generation). The modified information may then be sent via network 560 to user device 510 for display on UI application 512.

Figure 6B:
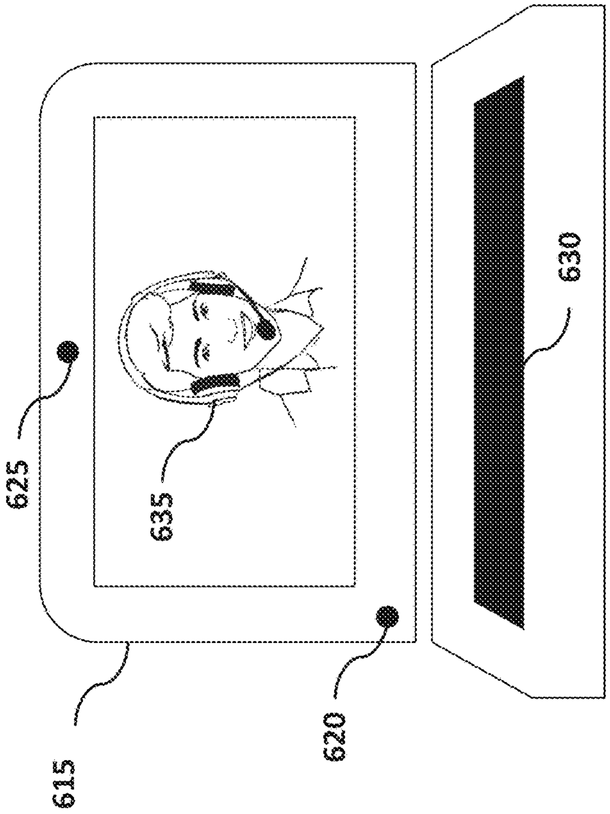
FIGS. 6A-6B are exemplary devices with digital avatar interfaces, according to some embodiments.
Figure 6A:
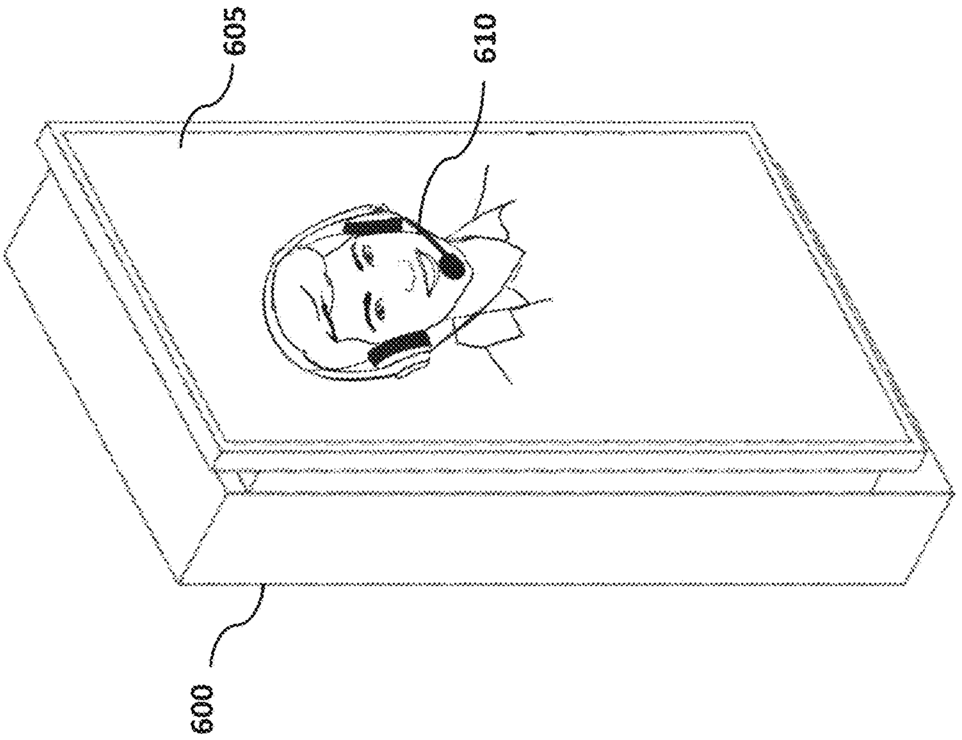

FIG. 6A is an exemplary device 600 with a digital avatar interface, according to some embodiments. Device 600 may be, for example, a kiosk that is available for use at a store, a library, a transit station, etc. Device 600 may display a digital avatar 610 on display 605. In some embodiments, a user may interact with the digital avatar 610 as they would a person, using voice and non-verbal gestures. Digital avatar 610 may interact with a user via digitally synthesized gestures, digitally synthesized voice, etc. Further, as described herein, device 600 may be configured to display avatar 610 to represent the gestures and voice (or modified version of voice) of a person.

Device 600 may include one or more microphones, and one or more image-capture devices (not shown) for user interaction. Device 600 may be connected to a network (e.g., network 560). Digital Avatar 610 may be controlled via local software and/or through software that is at a central server accessed via a network. For example, an AI model may be used to control the behavior of digital avatar 610, and that AI model may be run remotely. In some embodiments, device 600 may be configured to perform functions described herein (e.g., via digital avatar 610). For example, device 600 may perform one or more of the functions as described with reference to computing device 300 or user device 510. For example, providing a continuity of care between an AI-based system and an expert-controlled system.

FIG. 6B is an exemplary device 615 with a digital avatar interface, according to some embodiments. Device 615 may be, for example, a personal laptop computer or other computing device. Device 615 may have an application that displays a digital avatar 635 with functionality similar to device 600. For example, device 615 may include a microphone 620 and image capturing device 625, which may be used to interact with digital avatar 635. In addition, device 615 may have other input devices such as a keyboard 630 for entering text.

Digital avatar 635 may interact with a user via digitally synthesized gestures, digitally synthesized voice, etc. Further, as described herein, device 615 may be configured to display avatar 635 to represent the gestures and voice (or modified version of voice) of a person. In some embodiments, device 615 may be configured to perform functions described herein (e.g., via digital avatar 635). For example, device 615 may perform one or more of the functions as described with reference to computing device 300 or user device 510. For example, providing a continuity of care between an AI-based system and an expert-controlled system.

Figure 7:
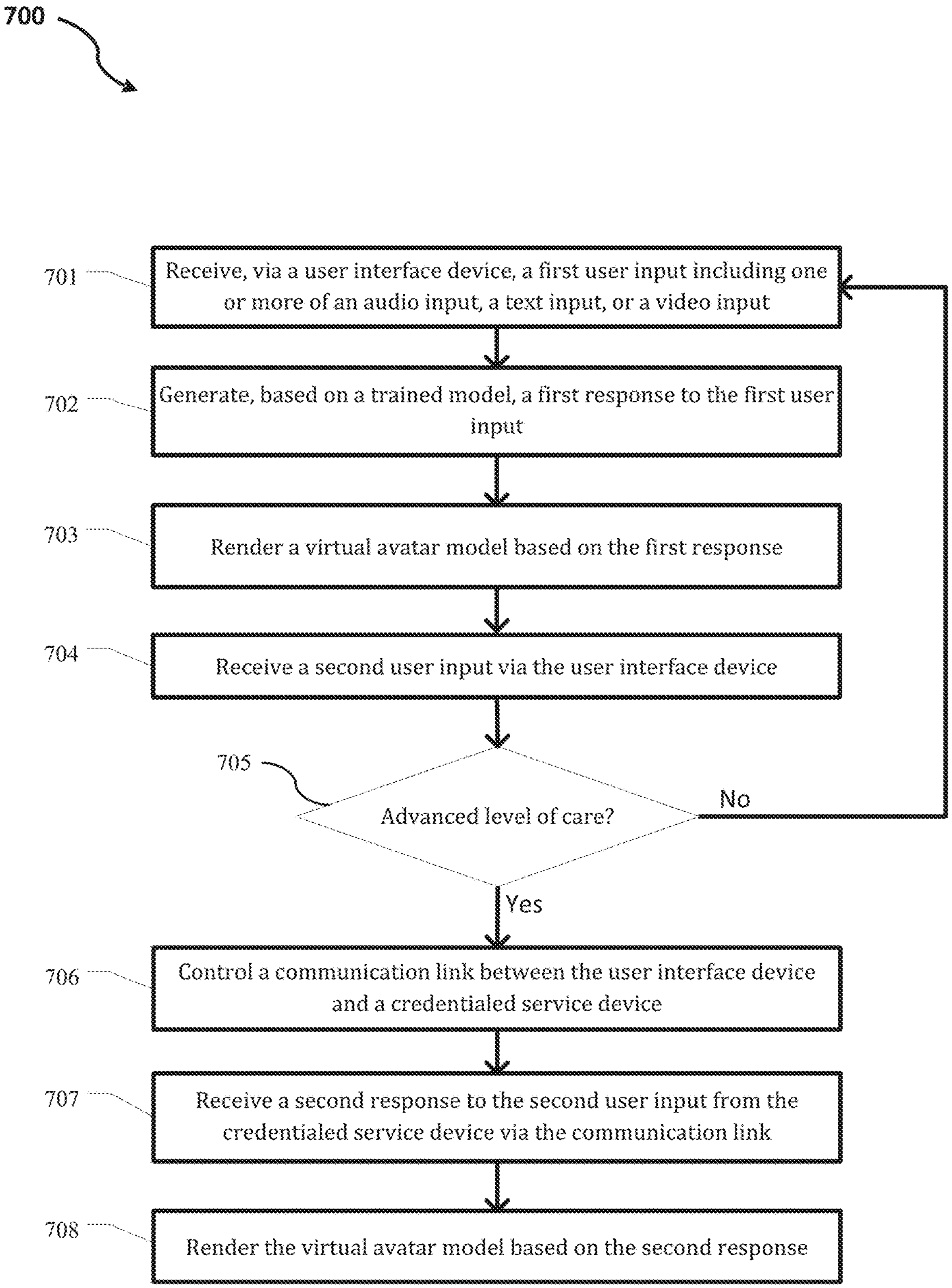
FIG. 7 is an example logic flow diagram, according to some embodiments.

FIG. 7 is an example logic flow diagram, according to some embodiments described herein. One or more of the processes of method 700 may be implemented, at least in part, in the form of executable code stored on non-transitory, tangible, machine-readable media that when run by one or more processors may cause the one or more processors to perform one or more of the processes (e.g., computing device 300). In some embodiments, method 700 corresponds to the operation of the AI avatar module 330 that generates and renders avatar-based responses to user inputs either via a trained model, or based on inputs from a credentialed user.

As illustrated, the method 700 includes a number of enumerated steps, but aspects of the method 700 may include additional steps before, after, and in between the enumerated steps. In some aspects, one or more of the enumerated steps may be omitted or performed in a different order.

At step 701, a system (e.g., edge device 125, system 202, computing device 300, user device 510, model server 540, device 600, or device 615) receives, via a user interface a first user input (e.g., a spoken question) including one or more of an audio input, a text input, or a video input. In some embodiments, receiving the first user input includes receiving the first user input via a network (e.g., network 130 or network 560).

At step 702, the system generates, based on a trained model (e.g., a large language model, a retrieval augmented generation model), a first response to the first user input.

At step 703, the system renders a virtual avatar model based on the first response. For example, gestures may be generated via a gesture generation model, and voice may be generated via a text-to-speech model. In some embodiments, rendering the virtual avatar model includes transmitting information to the user interface device via the network. For example, the system may be a server such as model server 540, and the avatar generated by model server 540 my be rendered by generating the gestures and voice of the model on model server 540 and transmitting the avatar information to user device 510 for display. In some embodiments, rendering the virtual avatar model based on the first response includes generating auditory speech of the first response in a first style.

At step 704, the system receives a second user input via the user interface device.

At step 705, the system determines whether to provide an advanced level of care. If the system determines to provide and advanced level of care, the system proceeds to step 706. If the system does not determine to provide an advanced level of care, the system may continue to perform steps 701-704 reacting to user inputs without the advanced level of care. The system may determine to provide an advanced level of care, for example, based on the second user input requiring a licensed professional to respond (e.g., providing a prescription or specific medical advice, etc.). In another example, the system may determine to provide an advanced level of care based on the system being unable to confidently respond to the second user input. In another example, the system may determine to provide an advanced level of case based on the second user input including an explicit request for the advanced level of care.

At step 706, the system controls a communication link between the user interface device and a credentialed service device (e.g., provider device 580).

At step 707, the system receives a second response to the second user input from the credentialed service device via the communication link. In some embodiments, the second response includes auditory speech in a second style (e.g., in the style spoken by the credentialed user).

At step 708, the system renders the virtual avatar model based on the second response. For example, a model may map the credentialed user's gestures to the avatar and/or convert the credentialed user's speech to match the voice style of the avatar. In another example, a text response from the credentialed user may be the basis of rendering the avatar by a gesture generation model and a text-to-speech model. In some embodiments, rendering the virtual avatar model includes determining a gesture based on the second response, wherein the rendering the avatar is further based on the gesture. For example, the rendered virtual avatar gesture may mimic a gesture of the credentialed user detected via a camera sensor. In some embodiments, rendering the virtual avatar model based on the second response includes converting the auditory speech of the second response to the first style. In some embodiments, the second response includes a text response, and the rendering the virtual avatar model based on the second response includes generating auditory speech of the second response in the first style.

The devices described above may be implemented by one or more hardware components, software components, and/or a combination of the hardware components and the software components. For example, the device and the components described in the exemplary embodiments may be implemented, for example, using one or more general purpose computers or special purpose computers such as a processor, a controller, an arithmetic logic unit (ALU), a digital signal processor, a microcomputer, a field programmable gate array (FPGA), a programmable logic unit (PLU), a microprocessor, or any other device which executes or responds instructions. The processing device may perform an operating system (OS) and one or more software applications which are performed on the operating system. Further, the processing device may access, store, manipulate, process, and generate data in response to the execution of the software. For ease of understanding, it may be described that a single processing device is used, but those skilled in the art may understand that the processing device includes a plurality of processing elements and/or a plurality of types of the processing element. For example, the processing device may include a plurality of processors or include one processor and one controller. Further, another processing configuration such as a parallel processor may be implemented.

The software may include a computer program, a code, an instruction, or a combination of one or more of them, which configure the processing device to be operated as desired or independently or collectively command the processing device. The software and/or data may be interpreted by a processing device or embodied in any tangible machines, components, physical devices, computer storage media, or devices to provide an instruction or data to the processing device. The software may be distributed on a computer system connected through a network to be stored or executed in a distributed manner The software and data may be stored in one or more computer readable recording media.

The method according to the exemplary embodiment may be implemented as a program instruction which may be executed by various computers to be recorded in a computer readable medium. At this time, the medium may continuously store a computer executable program or temporarily store it to execute or download the program. Further, the medium may be various recording means or storage means to which a single or a plurality of hardware is coupled and the medium is not limited to a medium which is directly connected to any computer system, but may be distributed on the network. Examples of the medium may include magnetic media such as hard disk, floppy disks and magnetic tapes, optical media such as CD-ROMs and DVDs, magneto-optical media such as optical disks, and ROMs, RAMS, and flash memories to be specifically configured to store program instructions. Further, an example of another medium may include a recording medium or a storage medium which is managed by an app store which distributes application, a site and servers which supply or distribute various software, or the like.

To provide for interaction with a user, embodiments can be implemented on a computer having a display device and an input device, for example, a liquid crystal display (LCD) or organic light-emitting diode (OLED)/virtual-reality (VR)/augmented-reality (AR) display for displaying information to the user and a touchscreen, keyboard, and a pointing device by which the user can provide input to the computer. Other kinds of devices can be used to provide for interaction with a user as well; for example, feedback provided to the user can be any form of sensory feedback, for example, visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

Embodiments can be implemented using computing devices interconnected by any form or medium of wireline or wireless digital data communication (or combination thereof), for example, a communication network. Examples of interconnected devices are a client and a server generally remote from each other that typically interact through a communication network. A client, for example, a mobile device, can carry out transactions itself, with a server, or through a server, for example, performing buy, sell, pay, give, send, or loan transactions, or authorizing the same. Such transactions may be in real time such that an action and a response are temporally proximate; for example an individual perceives the action and the response occurring substantially simultaneously, the time difference for a response following the individual's action is less than 1 millisecond (ms) or less than 1 second(s), or the response is without intentional delay taking into account processing limitations of the system.

Examples of communication networks include a local area network (LAN), a radio access network (RAN), a metropolitan area network (MAN), and a wide area network (WAN). The communication network can include all or a portion of the Internet, another communication network, or a combination of communication networks. Information can be transmitted on the communication network according to various protocols and standards, including Long Term Evolution (LTE), 5G, IEEE 802, Internet Protocol (IP), or other protocols or combinations of protocols. The communication network can transmit voice, video, biometric, or authentication data, or other information between the connected computing devices.

Features described as separate implementations may be implemented, in combination, in a single implementation, while features described as a single implementation may be implemented in multiple implementations, separately, or in any suitable sub-combination. Operations described and claimed in a particular order should not be understood as requiring that the particular order, nor that all illustrated operations must be performed (some operations can be optional). As appropriate, multitasking or parallel-processing (or a combination of multitasking and parallel-processing) can be performed.

Although the exemplary embodiments have been described above by a limited embodiment and the drawings, various modifications and changes can be made from the above description by those skilled in the art. For example, even when the above-described techniques are performed by different order from the described method and/or components such as systems, structures, devices, or circuits described above are coupled or combined in a different manner from the described method or replaced or substituted with other components or equivalents, the appropriate results can be achieved. It will be understood that many additional changes in the details, materials, steps and arrangement of parts, which have been herein described and illustrated to explain the nature of the subject matter, may be made by those skilled in the art within the principle and scope of the invention as expressed in the appended claims.

What is claimed is:

1. A method comprising:

receiving, via a user interface device, a first user input including one or more of an audio input, a text input, or a video input;

generating, based on a trained model, a first response to the first user input;

rendering a virtual avatar model based on the first response;

receiving a second user input via the user interface device; and determining, based on the second user input, to provide an advanced level of care including:

controlling a communication link between the user interface device and a service device operated by a credentialed user, wherein the communication link comprises a private channel;

receiving a second response to the second user input from the service device operated by the credentialed user via the private channel, and rendering the virtual avatar model based on the second response.

2. The method of claim 1, wherein:

receiving the first user input includes receiving the first user input via a network; and rendering the virtual avatar model includes transmitting information to the user interface device via the network.

3. The method of claim 1, wherein rendering the virtual avatar model includes determining a gesture based on the second response, wherein the rendering the avatar is further based on the gesture.

4. The method of claim 1, wherein the rendering the virtual avatar model based on the first response includes generating auditory speech of the first response in a first style associated with the virtual avatar model.

5. The method of claim 4, wherein:

the second response includes auditory speech in a second style captured at the service device from the credentialed user, and the rendering the virtual avatar model based on the second response includes converting the auditory speech of the second response to the first style associated with the virtual avatar model.

6. The method of claim 4, wherein:

the second response includes a text response provided by the credentialed user via the service device, and the rendering the virtual avatar model based on the second response includes generating auditory speech of the second response in the first style associated with the virtual avatar model.

7. The method of claim 1, wherein the rendering the virtual avatar model includes causing to be presented, via the user interface device, at least one of audio, text, images, or video.

8. A computing device comprising:

one or more memories storing instructions; and one or more processors coupled to the one or more memories and configured, individually or in any combination, to execute the instructions to cause the computing device to:

receive, via a user interface device, a first user input including one or more of an audio input, a text input, or a video input;

generate, based on a trained model, a first response to the first user input;

render a virtual avatar model based on the first response;

receive a second user input via the user interface device; and determine, based on the second user input, to provide an advanced level of care including:

control a communication link between the computing device and a service device operated by a credentialed user, wherein the communication link comprises a private channel;

receive a second response to the second user input from the service device operated by the credentialed user via the private channel, and render the virtual avatar model based on the second response.

9. The computing device of claim 8, wherein the one or more processors are further configured to cause the computing device to:

receive the first user input via a network, transmit information to the user interface device via the network associated with the rendered virtual avatar model.

10. The computing device of claim 8, wherein the one or more processors are further configured to cause the computing device to:

determine a gesture based on the second response; and render avatar based on the gesture.

11. The computing device of claim 8, wherein the one or more processors are further configured to cause the computing device to:

generate auditory speech of the first response in a first style associated with the virtual avatar model and render the virtual avatar model based on the generated auditory speech.

12. The computing device of claim 11, wherein the second response includes auditory speech in a second style captured at the service device from the credentialed user, and wherein the one or more processors are further configured to cause the computing device to:

convert the auditory speech of the second response to the first style associated with the virtual avatar model; and render the virtual avatar model based on the converted auditory speech.

13. The computing device of claim 11, wherein the second response includes a text response provided by the credentialed user via the service device, and wherein the one or more processors are further configured to cause the computing device to:

generate auditory speech of the second response in the first style associated with the virtual avatar model; and render the virtual avatar model based on the generated auditory speech.

14. The computing device of claim 8, wherein the rendering the virtual avatar model includes causing to be presented, via the user interface device, at least one of audio, text, images, or video.

15. A non-transitory computer readable medium including program code, the program code operable, when executed by one or more processors, to perform operations comprising:

receiving, via a user interface device, a first user input including one or more of an audio input, a text input, or a video input;

generating, based on a trained model, a first response to the first user input;

rendering a virtual avatar model based on the first response;

receiving a second user input via the user interface device; and determining, based on the second user input, to provide an advanced level of care including:

controlling a communication link between the user interface device and a service device operated by a credentialed user, wherein the communication link comprises a private channel;

receiving a second response to the second user input from the service device operated by the credentialed user via the private channel, and rendering the virtual avatar model based on the second response.

16. The non-transitory computer readable medium of claim 15, wherein:

receiving the first user input includes receiving the first user input via a network; and rendering the virtual avatar model includes transmitting information to the user interface device via the network.

17. The non-transitory computer readable medium of claim 15, wherein rendering the virtual avatar model includes determining a gesture based on the second response, wherein the rendering the avatar is further based on the gesture.

18. The non-transitory computer readable of claim 15, wherein the rendering the virtual avatar model based on the first response includes generating auditory speech of the first response in a first style associated with the virtual avatar model.

19. The non-transitory computer readable medium of claim 18, wherein:

the second response includes auditory speech in a second style captured at the service device from the credentialed user, and the rendering the virtual avatar model based on the second response includes converting the auditory speech of the second response to the first style associated with the virtual avatar model.

20. The non-transitory computer readable medium of claim 18, wherein:

the second response includes a text response provided by the credentialed user via the service device, and the rendering the virtual avatar model based on the second response includes generating auditory speech of the second response in the first style associated with the virtual avatar model.

* * * * *